United States Patent [19]

Cousse et al.

[11] 4,152,521
[45] May 1, 1979

[54] β-NICOTINAMIDO-ETHYL ANTHRANILATE

[75] Inventors: Henri Cousse; Gilbert Mouzin, both of Castres, France

[73] Assignee: Pierre Fabre S.A., France

[21] Appl. No.: 931,488

[22] Filed: Aug. 7, 1978

Related U.S. Application Data

[62] Division of Ser. No. 749,230, Dec. 10, 1976.

[30] Foreign Application Priority Data

Dec. 19, 1975 [FR] France .................................. 75 39410

[51] Int. Cl.² ........................................... C07D 213/56
[52] U.S. Cl. .................................................. 546/316
[58] Field of Search ................ 260/295.5 A, 295 AM

[56] References Cited

U.S. PATENT DOCUMENTS 4,021,436  5/1977  Cavazza ........................ 260/294.8 E

OTHER PUBLICATIONS

Bailey et al., Chem. Abstracts, vol. 77 (2), 14,181m, Jul. 10, 1972.

Primary Examiner—Alan L. Rotman
Attorney, Agent, or Firm—Gordon W. Hueschen

[57] ABSTRACT

The invention concerns new chemical compounds which can be used as medicaments, their preparation, and pharmaceutical compositions, and method of treating therewith.

The new chemical compounds have the general formula

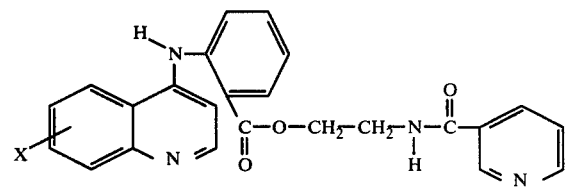

in which X, which is in 7 position, represents a halogen atom or a trifluoromethyl group.

The medicaments containing these active principles may be used in the treatment of various pains, i.e., as analgesics.

1 Claim, No Drawings

β-NICOTINAMIDO-ETHYL ANTHRANILATE

This is a division of application Ser. No. 749,230, filed Dec. 10, 1976.

BACKGROUND OF INVENTION

Field of Invention

New chemical compounds, β-nicotinamidoethyl-N-(7-halo or trifluoromethyl-4-quinolyl)-anthranilates, analgesics, compositions thereof, method of treating therewith.

SUMMARY OF THE INVENTION

The present invention relates to certain new chemical compounds, which are β-nicotinamidoethyl-N-(7-halo or trifluoromethyl-4-quinolyl)-anthranilates, in the form of free bases and salts thereof, which are useful an analgesics, pharmaceutical compositions thereof, and method of treating therewith.

OBJECTS

It is accordingly an object of the present invention to provide certain novel β-nicotinamidoethyl-N-(7-halo or trifluoromethyl-4-quinolyl)-anthranilates, acid addition salts thereof, pharmaceutical compositions of the same in the form of either the free base or an acid addition salt thereof, and a method of treating therewith, especially a method of treating or ameliorating pains therewith. Another object is the provision of novel analgesic agents, compositions thereof, and method of treating therewith. Still other objects will become apparent hereinafter and additional objects will be obvious to one skilled in the art.

THE INVENTION

The present invention, made at the Pierre FABRE Research Center, relates to new derivatives of 4-amino quinoline, their salts with pharmaceutically acceptable inorganic or organic acids, their preparation, and their use in therapy, particularly for the treatment of various pains.

The invention also relates to pharmaceutical compositions which contain these active principles.

The new chemical compounds have the general formula

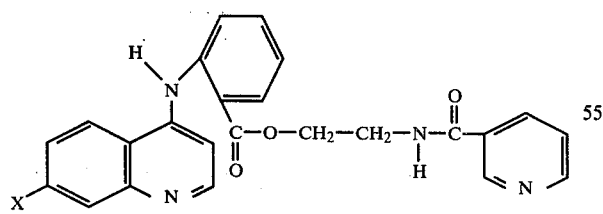

in which X in 7 position represents a halogen atom or a trifluoromethyl group.

The process for the preparation of these compounds comprises reacting a derivative of quinoline with β-nicotinamidoethyl anthranilate, this ester being in its turn obtained by the action of N(2-hydroxyethyl)-nicotinamide on isatoic anhydride in accordance with the following reaction mechanism:

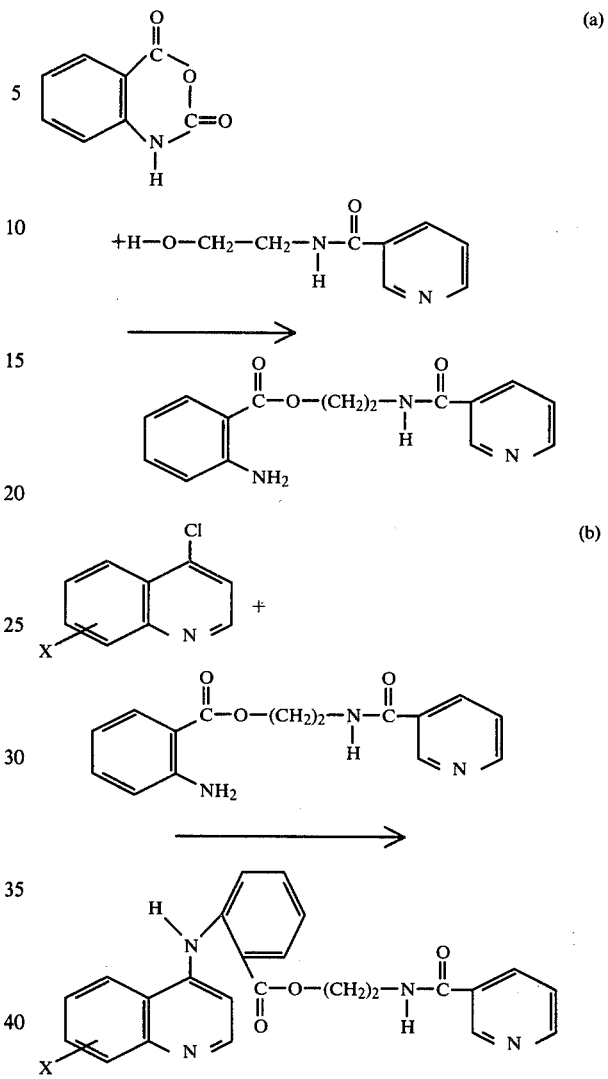

X having the meaning indicated above.

DETAILED DESCRIPTION OF THE INVENTION

The following Examples are given by way of illustration only and are not to be construed as limiting.

The following new chemical compounds and their method of preparation are indicated by way of illustration and not of limitation.

EXAMPLE 1

β-nicotinamido-ethyl anthranilate

Introduce 1344 g (8.3 m) of isatoic anhydride, 5 liters of dioxane, 1328 g (8 m) of N(hydroxy ethyl)-nicotinamide, and 48 g (1.2 m) of sodium hydroxide into a 10 liter reactor.

Heat for 2 hours at 80° C. A liberation of a substantial amount of $CO_2$ is noted. Expel the dioxane under vacuum from the precipitated anthranilate.

Add 5 liters of water and filter.

Upon drying there is recovered 90% of a compound of the formula

[Structure: 2-aminobenzoate-CO2-CH2-CH2-NH-C(=O)-pyridyl]

which has the following properties:

Empirical formula: $C_{15}H_{15}N_3O_3$
Molecular weight: 285.3
Melting point: 133° C.
Infrared spectrography:  $\delta C=C$ (aromatic) at 1575 cm$^{-1}$
  $\delta C=O$ (acid) at 1630 cm$^{-1}$
  $\delta C=O$ (ester) at 1680 cm$^{-1}$
Thin-layer chromatography:
  -support: silica gel
  -solvent: ethyl acetate
  -development: UV and iodine
  -Rf: 0.28

Solubility characteristics: insoluble in water. 2.5% soluble in alcohol, 100% soluble in dimethyl acetamide.

EXAMPLE 2

β-nicotinamido-ethyl-N(7-chloro 4-quinolyl)-anthranilate—F 1531

Introduce 1072 g (3.77 m) of β-nicotinamido-ethyl anthranilate, 4.5 liters of ethanol, and 800 g of 4,7-dichloroquinoline hydrochloride (3.4 mols) into a 10 liter reactor.

Agitate the reaction mixture, and heat under reflux for 6 hours. The β-nicotinamido-ethyl-N(7-chloro 4-quinolyl)-anthranilate hydrochloride formed precipitates.

Filter, dissolve in 8 liters of water, and neutralize by addition of 584 g of sodium bicarbonate dissolved in 30 liters of water.

The free base, recovered by filtration, is recrystallized in 12 liters of chloroform.

85% product is recovered, of the formula

[Structure: 7-chloro-4-quinolyl-NH-phenyl-CO2-CH2-CH2-NH-C(=O)-pyridyl]

which has the following analytical characteristics:

Empirical formula: $C_{24}H_{19}ClN_4O_3$
Molecular weight: 446.9
Melting point: 174° C.
Percentage analysis: corresponds
Infrared spectrum:  $\delta C=C$ (aromatic) at 1575 cm$^{-1}$
  $\delta C=O$ (amide) at 1620 cm$^{-1}$
  $\delta C=O$ (ester) at 1680 cm$^{-1}$
Thin-layer chromatography:
  -support: silica gel
  -solvent: bytanol/AcOH/H2O 6/2/2
  -development: UV and iodine
  -Rf: 0.57

Solubility characteristics: 20% soluble in a (N) solution of hydrochloric acid.

In the same manner as given in the foregoing, by substitution of the appropriate 4,7-dihaloquinoline starting material for the 4,7-dichloroquinoline hydrochloride employed in the foregoing Example 2, for example, the 4,7-dibromoquinoline hydrobromide, 4-bromo or chloro,7-fluoroquinoline hydrochloride, and 4,7-diidoquinoline hydroiodide, the corresponding compounds are obtained, namely:

β-nicotinamido-ethyl-N(7-bromo 4-quinolyl)-anthranilate

β-nicotinamido-ethyl-N(7-fluoro 4-quinolyl)-anthranilate

β-nicotinamido-ethyl-N(7-iodo 4-quinolyl)-anthranilate

In the same manner, innumerable other acid addition salts are also prepared, e.g., the methanesulfonates, tartrates, and phosphates.

EXAMPLE 3

β-nicotinamido-ethyl-N(7-trifluoromethyl-4-quinolyl)-anthranilate—F 1636

Introduce 2.77 kg of β-nicotinamido-ethyl anthranilate, 2.47 kg of 4-chloro-7-trifluoromethyl quinoline, and 25 liters of (N) hydrochloric acid into a 50 liter reactor.

Heat at 80° C. for a few hours, allow to cool to room temperature, and neutralize the hydrochloride salt thus produced with a solution of bicarbonated water to form the free base.

(In the same manner, innumerable other acid addition salts are also prepared, e.g., the hydrobromide, oxalate, and citrate.)

Filter, wash with water, and recrystallize from ethanol.

There are recovered 3.78 kg of product (yield about 80%) of the formula

[Structure: 7-CF3-4-quinolyl-NH-phenyl-C(=O)-O-CH2-CH2-NH-C(=O)-pyridyl]

which has the following analytical characteristics:

Empirical formula: $C_{25}H_{19}F_3N_4O_3$
Molecular weight: 480.45
Melting point: 191° C.
Percentage analysis: corresponds
Infrared spectrography  $\delta C=C$ (aromatic) at 1575 cm$^{-1}$
  $\delta C=O$ (amide) at 1615 cm$^{-1}$
  $\delta C=O$ (ester) at 1665 cm$^{-1}$
Thin-layer chromatography:
  -support: silica gel
  -solvent: butanol - acetic acid - water 6/2/2
  -development: UV and iodine -Rf: 0.71

Solubility characteristics: 8% soluble in dimethyl formamide.

EXPERIMENTS

For the sake of convenience, the chemical compounds subjected to the experiments are designated by a code number.

The tests described below relate to β-nicotinamido-ethyl-N(7-chloro-4-quinolyl)-anthranilate designated by the code number F 1531 and β-nicotinamido-ethyl-N(7-trifluoromethyl-4-quinolyl)-anthranilate, F 1636.

(A) Toxicology

The toxicology study was carried out on the conventional mouse weighing about 20 g.

The substances were administered orally and intraperitoneally. The $LD_{50}$ is calculated by the method of MILLER and TAINTER (Proc. Soc. Exper. Biol. Med. 1944, 57, 261).

| Compound | Orally mg/kg | Intraperitoneally mg/kg |
|---|---|---|
| Glaphenine | 1500 ± 500 | ≃ 500 |
| F 1531 | 2800 ± 500 | >500 |
| F 1636 | 3200 ± 500 | >1000 |

(B) Pharmacodynamics

The pharmacological tests showed the following properties:

(1.) Analgesic activity (a) Studied by the technique of SIEGMUND et al. (J. Pharmacol. Exptl. Therap. 1957, 119, 453).

The compounds are administered orally 30 minutes before the injection of the phenyl benzoquinone solution.

| Compounds | $ED_{50}$ |
|---|---|
| Aspirin | 100 mg/kg |
| Glaphenine | 36 mg/kg |
| F 1531 | 28 mg/kg |
| F 1636 | 15 mg/kg |

(b) Electrical stimulation of rabbit tooth in accordance with CHEYMOL—Therapie 1959, XIV, p. 350 to 360. The two products F 1531 and F 1636 show better activity than the control product (glaphenine); in a dose of 100 mg/kg, administered orally, the maximum activity occurs about 60 minutes after administration.

(2.) Ulcerogenic properties in rats

The ulceration index was determined in rats subjected to constraint for 7 hours.

The compound is administered orally in a volume of 10 ml/kg to male animals of a weight of 200 to 230 g who have fasted for 24 hours.

The vehicle is a 4% aqueous solution of Tween 80 (TM —surface active agent).

The ulcerogenic index is calculated in accordance with the criteria established by PFEIFFER et al. (Arch. Int. Pharmacodyn. 1971, 190, 6–13).

| Compounds | dose | N | Ulceration index | standard error |
|---|---|---|---|---|
| Vehicle | 5 ml/kg | 10 | 2.2 | ± 0.2 |
| F 1531 | 100 | 10 | 5.3 | ± 0.65 |
| F 1636 | 100 | 10 | 4.2 | ± 0.6 |
| Glaphenine | 100 | 10 | 8.8 | ± 1.10 |
| Aspirin | 300 | 10 | 13.1 | ± 1.50 |

(3.) Absence of central properties

The doses of F 1531, resulting in the falling of mice placed on a horizontal bar of scraped wood of 4 cm diameter and turning at 8 rpm, are identical with the lethal doses. The same is true of the doses resulting in the loss of the contraction reflex.

In the study of the potentialization of the anesthesia induced by 350 mg/kg of chloral hydrate (intraperitoneally) in mice, the dose of 100 mg/kg of F 1531, administered orally 30 minutes in advance, results in neither potentialization nor decrease in the anesthesia as compared with the controls treated by the vehicle. Same remarks for F 1636.

(C) Therapeutic uses

In view of excellent tolerance of the new chemical compounds, clinical tests were carried out on volunteers with respect to certain compounds forming the object of the invention.

Thus after having carried out subacute and chronic toxicity studies on animals, the compounds F 1531 and F 1636 were used for various experimentations in the case of stubborn pains, particularly those amenable to prolonged treatment.

The initial results proved satisfactory.

The pharmaceutical preparations containing these active principles were administered orally, parenterally, rectally, and locally.

For oral administration tablets, capsules and elixirs were used, the unit dose being 50 to 500 mg, in accordance with a maximum daily dose of 1800 mg. For rectal administration these quantities are 100 to 800 mg respectively.

These pharmaceutical compositions may also contain other pharmaceutically and therapeutically compatible active principles.

A few examples of pharmaceutical preparations which contain the active principle forming the object of the experiment are given below, by way of illustration and not of limitation:

(a) tablets F 1531  150 mg
    excipient
(b) suppository, adult, strong: F 1531  200 mg/suppository
    excipient
(c) capsules: F 1636  75 mg
    Meprobamate 100 mg; or F 1636 alone The new derivatives obtained in the foregoing manner, which are bases, can be converted into addition salts with acids, which form part of the invention. The addition salts can be obtained by the reaction of the new derivatives with acids in suitable solvents such, for example, as shown by the examples. As acids used for the formation of these addition salts there may be mentioned, in the mineral series: hydrochloric, hydrobromic, methanesulphonic, sulphuric and phosphoric acid; in the organic series: acetic, propionic, maleic, fumaric, tartaric, citric, oxalic, benzoic acid, to name a few.

The invention accordingly also relates to the salts with organic or inorganic acids, especially lipophilic acids, e.g., fatty acids having 14 to 22 carbon atoms, inclusive, which are linear or branched, saturated or unsaturated, including palmitic, linoleic, linolenic, and oleic acids, and the like, as well as of the naphthoic type, especially pamoic acid, in addition to the usual organic and inorganic acids of the type already mentioned.

The selection of the free base or acid addition salt thereof and preparation of the desired acid addition salt of a compound in any particular case will be apparent and fully within the ability of one skilled in the art.

The novel compounds are frequently used in the form of their pharmaceutically-acceptable acid addition salts, e.g., their hydrochlorides, hydrobromides, or the like. The salt is usually the best form for pharmaceutical formulations. Innumerable other pharmaceutically-acceptable acid addition salts can be prepared from the hydrochlorides via the free bases in conventional manner. For oral use, the compounds are usually administered as tablets, solutions, or suspensions, in which they are present together with usual pharmaceutical carriers, excipients, binders, and the like. For example, tablets may be prepared conventionally by compounding one of the new compounds, preferably in the form of an acid addition salt thereof, with customary carriers and adjuvants, e.g., talc, magnesium stearate, starch, lactose, gelatin, gums, and the like. In their most advantageous form, then, the compositions of the present invention will contain a non-toxic pharmaceutical carrier in addition to the active ingredient. Exemplary carriers are:

Solids: lactose, magnesium stearate, calcium stearate, starch, terra alba, dicalcium phosphate, sucrose, talc, stearate acid, gelatin, agar, pectin, acacia, or other usual excipient;

Liquids: peanut oil, sesame oil, olive oil, water, elixir, or other usual excipient. The active agents of the invention can be most conveniently administered in such compositions containing about 0.01 to 67 percent, preferably 0.04 to 12.15 percent, by weight of the active ingredient. Such formulations are representatively illustrated in U.S. Pat. No. 3,402,244.

A wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion; and for rectal administration, a suppository.

The method of using the compounds of the present invention comprises internally administering a compound of the invention, usually in the form of a non-toxic, pharmacologically-acceptable acid addition salt, and preferably admixed with a pharmaceutical carrier, for example, in the form of any of the above-mentioned compositions, or filled into a capsule, to alleviate one or more of the foregoing enumerated conditions and symptoms in a living animal body, whether human or domestic animal, for example, the aforementioned pains. The compounds are subject to usual variations in optimum daily and unit dosages, due to patient body weight, condition, and ancillary factors, and the invention therefore should not be limited by the exact ranges stated. The exact dosage, both unit and daily, will of course have to be determined according to established veterinary and medical principles.

General

The free bases of the invention may generally be extracted with a suitable organic solvent, e.g., ether, methyl-butyl ketone, or the like, if desired. Salts with pharmaceutically acceptable acids, e.g., hydrochloric, hydrobromic, fumaric, citric, maleic, tartaric, or lactic, or the like, may also be precipitated with acid from a dried solution of the free base in a conventional manner and recrystallized. One acid salt, even if not pharmaceutically acceptable, is still useful, since it can readily be converted to another salt which is pharmaceutically acceptable in known manner, e.g., by alkalization and then acidification with a different acid, if desired.

Where chloro or other halogen atom is present, although chlorine is preferred, further halogen compounds including iodo, bromo, chloro, and fluoro compounds are prepared starting from the appropriate halogenated starting material.

It is to be understood that the invention is not to be limited to the exact details of the operation or exact compounds, compositions, or procedures shown and described, as obvious modifications and equivalents will be apparent to one skilled in the art, and the invention is therefore to be limited only by the scope of the appended claims.

We claim:

1. β-nicotinamido-ethyl anthranilate of the formula:

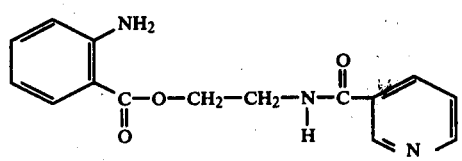

UNITED STATES PATENT AND TRADEMARK OFFICE
CERTIFICATE OF CORRECTION

PATENT NO. : 4,152,521

DATED : May 1, 1979

INVENTOR(S) : Cousse et al.

It is certified that error appears in the above-identified patent and that said Letters Patent are hereby corrected as shown below:

Col. 4, line 4; "bytanol/" should read -- butanol/ --
Col. 4, line 17; "diidoquinoline" should read -- diiodoquinoline --

Signed and Sealed this

Tenth Day of July 1979

[SEAL]

Attest:

LUTRELLE F. PARKER

Attesting Officer      Acting Commissioner of Patents and Trademarks